United States Patent [19]
Buchbinder

[11] 4,382,077
[45] May 3, 1983

[54] PESTICIDE FOGGING COMPOSITIONS AND SOLVENT THEREFOR

[75] Inventor: Emanuel Buchbinder, Beer-Sheva, Israel

[73] Assignee: Makhteshim Chemical Works Ltd., Beer-Sheva, Israel

[21] Appl. No.: 238,085

[22] Filed: Feb. 25, 1981

Related U.S. Application Data

[63] Continuation-in-part of Ser. No. 104,988, Dec. 18, 1979, abandoned.

[30] Foreign Application Priority Data

Dec. 29, 1978 [IL] Israel ........................................ 56337

[51] Int. Cl.$^3$ ...................... A01N 25/06; A01N 25/18; A01N 25/20; A01N 25/00
[52] U.S. Cl. ........................................ 424/40; 252/305; 424/200; 424/219; 424/225; 424/245; 424/250; 424/276; 424/300; 424/305; 424/358
[58] Field of Search ................. 424/40, 219, 200, 225, 424/245, 250, 276, 300, 358; 252/305

[56] References Cited

U.S. PATENT DOCUMENTS

| | | | |
|---|---|---|---|
| 2,321,023 | 6/1943 | Goodhue et al. | 252/305 |
| 2,694,712 | 11/1954 | Gysin et al. | 424/40 |
| 3,131,153 | 4/1964 | Klausner | 252/305 |
| 3,131,154 | 4/1964 | Klausner | 252/305 |
| 3,387,425 | 6/1968 | Flanner | 252/305 |

FOREIGN PATENT DOCUMENTS 15-13725  1/1940  Japan ................................. 252/305

OTHER PUBLICATIONS

Soap & Sanitary Chem.–Fulton et al., 24(5), pp. 125–127 and 157–158, (1948).
Aerosols: Science & Tech.–Sheppard–pp. 233 & 464, Inters. Publ. Inc.–New York, 1961.
Chem. Abst. 80, 14548(y), (1974)–Lolivier et al.
Chem. Abst. 81, 146915(w), (1974)–Kamata et al.

Primary Examiner—Douglas W. Robinson
Attorney, Agent, or Firm—Browdy and Neimark

[57] ABSTRACT

There is provided a solvent system for application of pesticides by fogging, said solvent system being of use with both liquid and solid (wettable powder) pesticides, said solvent system comprising in combination 38 to 80 parts by weight of a glycol or a glycol ether, from 2 to 20 parts by weight of an alcohol of 1 to 3 carbon atoms and 18 to 60 parts by weight of methylene chloride.

10 Claims, No Drawings

4,382,077

PESTICIDE FOGGING COMPOSITIONS AND SOLVENT THEREFOR

RELATION TO PRIOR PATENT APPLICATION

This patent application is a continuation-in-part patent application to U.S. patent application Ser. No. 104,988 filed on Dec. 18, 1979, now abandoned without prejudice in favor of the present application.

FIELD OF THE INVENTION

This invention concerns pesticide compositions for use in fogging applications. More particularly, this invention is concerned with a novel solvent system for pesticides which can be used effectively in fogging compositions wherein the pesticide concentrate may be either solid or liquid.

BACKGROUND OF THE INVENTION

The common way of applying pesticides both outdoors in the field and indoors, for example in greenhouses and warehouses, is to spray the pesticide. These sprays are formulated for the particular application, and these formualations are prepared from a pesticide concentrate which is usually diluted with water or solvent prior to spraying. These pesticide concentrates may be 100% active ingredient, liquid or powder, or they can be solutions containing active pesticide from 20 to 95% in solvents, or they may be emulsifiable concentrates containing various percentages of active ingredient, or they may also be wettable powders. These concentrates are subsequently diluted with water and sometimes with other solvents and thus sprayed on to the plants or fields.

This spraying method has a number of drawbacks that make it undesirable. For one thing, spray particles settle on horizontal surfaces and leave unsightly residue. Furthermore, there is always a possibility of accumulating harmful chemical concentrations. The primary drawback of ordinary spraying, however, is that it is relatively inefficient and thus costly. This is because of the relatively large particle size of the spray drops. For example, a pesticidal particle of only five microns in size is adequate to kill an insect. Spraying produces particles of over 125 microns in size. Thus if we are able to get smaller particles they would be more efficient.

Aerosol sprays, which generally give finer particle size, are known for dispersing pesticides. They have, however, certain drawbacks. Aerosols are generally based on pressurized systems wherein a liquified gas is used to propel the pesticide into the atmosphere. These liquified gases are usually costly and also present handling problems. Furthermore, since the formulations must remain confined in a container under pressure until it is expanded there are certain safety risks.

One relatively new development in the application of pesticides is the concept of fogging. This is accomplished with an apparatus called a fogger which contains a tank for holding pesticide solutions or dispersions which are drawn into another section of the apparatus and flash evaporated by being heated with a very hot blast of air and forced through a nozzle. The hot air burns or consumes the solvents and spreads a thin dry mist and fog which covers a very large area.

Fogging offers a number of advantages over spraying one of which is smaller particle size. For example spraying can produce only about 225 million droplets from a quart of insecticide whereas fogging machines can break up insecticide to 14,000 billion effective particles per quart. This makes fogging approximately 65 times more efficient than spraying. Small particles not only make fogging more efficient than spraying but also more effective. Spray particles tend to settle on horizontal surfaces and with many sprays it is necessary for the pesticide to make contact with the insect. This means that if the pests, for example, in a warehouse or storage house are hidden under something like a carton or a box, the pesticide will never reach the pests. With fogging, however, because the particles are so small they remain airborne for longer periods of time and air currents carry them throughout the space of any indoor environment. The fog creeps under crates and crevices and makes contact with the pests whereever they may be. Another feature of pesticide fogs is that they leave no residue. Fogging produces particles of under 50 microns and while in the case of spraying you feel the wet spray, in fogging the fog is dry, and billions of micron size fog particles drift with air currents. The fogging also eliminates the danger of harmful chemical buildup. Some of the commercial foggers available are "London-Fog", "Dyna-Fog", and others. One key to the successful applications of a fog is the solvent or solvent system used to dissolve or disperse the pesticide concentrate for use in the foggers. The known solvents for fogging have been petroleum distillates, mixtures of ethylene glycol and methanol, mixtures of ethylene glycol monoethyl ether mixed with methanol and distilled water; a mixture of methylene dichloride and Risella oil. These solvent systems although useful have their limitations. Some of these are useful only with pesticide concentrate which are liquid, that is either solutions or emulsifiable concentrates, whereas others are only useful in formulations of wettable powders. None of them can be used as a universal solvent system for both liquid and solid pesticide concentrates.

Exterminators or applicators using fogging techniques have to either purchase ready made formulations for fogging specifically designed for each active ingredient, or they have to carry a stock of several different solvent systems for different types of concentrates if they wish to prepare their own fogging compositions.

Thus, there is a need for a single solvent system that can be offered to the end user for dissolving or dispersing both liquid and solid pesticide concentrates and yet giving excellent fogs.

SUMMARY OF THE INVENTION

We have discovered that the combination of glycols or glycol ethers, such as diethylene glycol plus alcohols of 1-3 carbon atoms such as methanol together with methylene dichloride provides solvent systems which not only are good for dissolving pesticide concentrates of all types but also provides excellent fog. Thus according to the present invention a solvent system comprising 40-80% diethyleneglycol, 2-30% methanol, and 18-60% methylene dichloride gives very good results. A more preferred ratio is 55% to 65% diethylene glycol, 5-15% methanol and 20-40% methylene dichloride. The pesticide formulation introduced into the fogger is usually about 60-99% solvent and the rest being pesticide concentrate. By pesticide concentrate we mean the pesticide formulation usually sold by the manufacturers to the consumers and these as stated earlier could be emulsifiable concentrates, wettable powders, solutions and other forms ready for formulating for final application. Such concentrates usually contain from 5–95% active pesticide.

In the case when using wettable powder concentrates for fogging applications, it is also helpful to introduce some water with the solvent system. For example a very convenient and successful formulation comprises about 75% solvent system, 15% pesticide concentrate as wettable powder, and 10% water. Slight variations of these ratios are, however, possible as well.

DESCRIPTION OF THE PREFERRED EMBODIMENT

Following are examples of formulations to be used in fogging applications:

EXAMPLE 1

A solvent system was prepared by mixing 60 parts diethyleneglycol 10 parts methanol and 30 parts methylene dichloride to form a solvent system specifically suitable for fogging applications.

The test for fogging efficiency was as follows:

A "Dynafog DH90" fogging apparatus was used to spread a fog into a 90 cubic meter room. 50 ml of fogging composition was thus applied. The density of the fog was visually estimated 10 seconds after application. A scale of from 0 to 100% was used to measure fog density, zero signifying no fog and 100% meaning total fog, or no visibility into the room. Partial densities were estimated respectively.

A comparison of commercial solvents for fogging formulations with the solvent composition of the invention as shown in Table 1, shows the advantage of the fog obtained with the composition of this invention

TABLE 1

| Solvent | Fog Density |
|---|---|
| Nevolin (1) | 60% |
| VK-2 (2) | 40% |
| Example 1 | 95% |

(1) A product of Chemische Pharmaceutische Div. "Luxan" Elst(GID) Holland.
(2) A product of Timmer Ltd. England, containing ethoxyethanol, methanol and water.

EXAMPLE 2

Pesticide concentrates were blended with the solvent system of Example 1 as follows:

A. 20% Aldicarb—80% solvent
B. 6% Naled—94% solvent
C. 6% DDVP—94% solvent
D. 20% Triforine—80% solvent
E. 25% Prodex—75% solvent
F. 35% Endosulfan 35EC—65% solvent
G. 10% Azinphos Methyl EC—90% solvent
H. 10% Diazinon-EC—90% solvent
I. 10% Actellic-EC—90% solvent
J. 10% Propoxur—90% solvent In all cases these formulations gave excellent fogs and were equal or superior to formulations of these pesticides prepared with commercial fogging solvents such as Nevolin, Pulsfog VK1 and Pulsfog VK2.

EXAMPLE 3

Wettable powder fogging compositions were prepared as follows giving excellent fogs.

75 parts of the solvent system of Example 1, 10 parts of water, and 15 parts of pesticide concentrate were mixed using the following pesticides:

(A) Maneb 80% W.P.
(B) Manzidan 80% W.P.
(C) Propineb 70% W.P.
(C) Carbaryl 85% W.P.

These fogging solutions were compared with formulations made with commercial solvents recommended for wettable powders such as Pulsfog VK2 and the inventive compositions were found to be much superior to the commercial products.

EXAMPLE 4

To demonstrate the versatility and universal applicability of the inventive solvent system for fogging applications a comparative study was made of four pesticides formulated with commercially recommended solvents for this technique and the inventive solvent system as well as with single and two solvent combinations of ingredients comprising the inventive three component solvent system.

The formulations were made up by blending 10 parts of pesticide concentrate with 90 parts of solvent.

The following concentrates were used.

(A) Naled-EC (liquid)
(B) Azinphos-EC (liquid)
(C) Maneb-WP (solid)
(D) Carbary-WP (solid)

The blended fogging formulations were measured for (1) flash point (2) viscosity (3) fogging ability and in the case of the liquid concentrates (4) solubility, and for solid concentrates (5) wetting and (6) suspensibility.

Ratings were assigned as follows:

1. satisfactory
2. insufficient/inadequate
3. unacceptable

The results are tabulated in Tables 2a (formulations with liquid concentrates) and 2b (formulations with solid concentrates).

From Tables 2a and 2b it is evident that only the inventive combination of solvents is satisfactory for formulating a variety of pesticides, both liquid and solid concentrates possessing the necessary desirable properties for successful fogging compositions.

TABLE 2a

| SOLVENT COMPOSITION (%) | PESTICIDE A (Liquid conc.) | | | | | | | | | | | |
|---|---|---|---|---|---|---|---|---|---|---|---|---|
| Diethylene Glycol | 100 | | | | | | | | 40 | 40 | 40 | |
| Methylenedichloride | | 100 | | | | | | | | 60 | | 50 |
| Methanol | | | 100 | | | | | | | | 60 | 50 |
| Petroleum Dist. | | | | 100 | | | | | 60 | | | |
| Pulsfog VK 1 | | | | | 100 | | | | | | | |
| Pulsfog VK 2 | | | | | | 100 | | | | | | |
| Nevolin | | | | | | | 100 | | | | | |
| Example 1 | | | | | | | | 100 | | | | |
| Solubility | 1 | 1 | 1 | 2 | 1 | 1 | 1 | 1 | 2 | 1 | 1 | 1 |
| Flash Point | 1 | 1 | 3 | 1 | — | — | — | 1 | 1 | 1 | 1 | 1 |
| Viscosity | 1 | 1 | 1 | 1 | 1 | 1 | 1 | 1 | 1 | 1 | 1 | 1 |

TABLE 2a-continued

| Fogging | 1 | 3 | 3 | 2 | 1 | 2 | 1 | 1 | 1 | 2 | 2 | 3 |
|---|---|---|---|---|---|---|---|---|---|---|---|---|
| SOLVENT COMPOSITION (%) | | | | | PESTICIDE B (Liquid conc.) | | | | | | | |
| Diethylene Glycol | 100 | | | | | | | | 40 | 40 | 40 | |
| Methylenedichloride | | 100 | | | | | | | | 60 | | 50 |
| Methanol | | | 100 | | | | | | | | 60 | 50 |
| Petroleum Dist. | | | | 100 | | | | | 60 | | | |
| Pulsfog VK 1 | | | | | 100 | | | | | | | |
| Pulsfog VK 2 | | | | | | 100 | | | | | | |
| Nevolin | | | | | | | 100 | | | | | |
| Example 1 | | | | | | | | 100 | | | | |
| Solubility | 2 | 1 | 1 | 2 | 1 | 1 | 1 | 1 | 3 | 1 | 1 | 1 |
| Flash Point | 1 | 1 | 3 | 1 | — | — | — | 1 | 1 | 1 | 2 | 1 |
| Viscosity | 1 | 1 | 1 | 1 | 1 | 1 | 1 | 1 | 1 | 1 | 1 | 1 |
| Fogging | 1 | 3 | 3 | 1 | 1 | 2 | 1 | 1 | 1 | 2 | 2 | 3 |

| SOLVENT COMPOSITION (%) | | | | | PESTICIDE C (WP) | | | | | | | |
|---|---|---|---|---|---|---|---|---|---|---|---|---|
| Diethylene Glycol | 100 | | | | | | | | 40 | 40 | 40 | |
| Methylenedichloride | | 100 | | | | | | | | 60 | | 50 |
| Methanol | | | 100 | | | | | | | | 60 | 50 |
| Petroleum Dist. | | | | 100 | | | | | 60 | | | |
| Pulsfog VK 1 | | | | | 100 | | | | | | | |
| Pulsfog VK 2 | | | | | | 100 | | | | | | |
| Nevolin | | | | | | | 100 | | | | | |
| Example 1 | | | | | | | | 100 | | | | |
| Flash Point | 1 | 1 | 3 | 2 | — | — | — | 1 | 1 | 1 | 3 | 1 |
| Viscosity | 3 | 1 | 1 | 2 | 2 | 1 | 1 | 1 | 2 | 1 | 1 | 1 |
| Fogging | 1 | 3 | 3 | 2 | 2 | 2 | 2 | 1 | 1 | 2 | 2 | 3 |
| Wetting | 2 | 2 | 1 | 2 | 2 | 1 | 1 | 1 | 2 | 2 | 1 | 1 |
| Suspensibility | 2 | 2 | 2 | 2 | 2 | 1 | 1 | 1 | 2 | 2 | 1 | 1 |

| SOLVENT COMPOSITION (%) | | | | | PESTICIDE D (WP) | | | | | | | |
|---|---|---|---|---|---|---|---|---|---|---|---|---|
| Diethylene Glycol | 100 | | | | | | | | 40 | 40 | 40 | |
| Methylenedichloride | | 100 | | | | | | | | 60 | | 50 |
| Methanol | | | 100 | | | | | | | | 60 | 50 |
| Petroleum Dist. | | | | 100 | | | | | 60 | | | |
| Pulsfog VK 1 | | | | | 100 | | | | | | | |
| Pulsfog VK 2 | | | | | | 100 | | | | | | |
| Nevolin | | | | | | | 100 | | | | | |
| Example 1 | | | | | | | | 100 | | | | |
| Flash Point | 1 | 1 | 3 | 2 | — | — | — | 1 | 1 | 1 | 3 | 1 |
| Viscosity | 3 | 1 | 1 | 2 | 2 | 1 | 2 | 1 | 2 | 1 | 1 | 1 |
| Fogging | 1 | 3 | 3 | 2 | 2 | 2 | 2 | 1 | 1 | 2 | 2 | 3 |
| Wetting | 2 | 1 | 1 | 2 | 2 | 1 | 2 | 1 | 2 | 1 | 1 | 2 |
| Suspensibility | 2 | 2 | 1 | 1 | 2 | 1 | 2 | 1 | 3 | 1 | 1 | 2 |

We claim:

1. A pesticidal fogging composition for application by a fogging device operating on thermal evaporation of the solvents, said composition comprising 1 to 40 parts by weight of the composition of a liquid or solid pesticide concentrate capable of being applied by fogging, dissolved or dispersed in a solvent system consisting essential of 38 to 80 parts glycol or a glycol ether solvent, 2 to 20 parts of an alcohol having 1 to 3 carbon atoms and 18 to 60 parts methylene dichloride.

2. A composition according to claim 1, wherein said solvent system consists essentially of 38 to 80 parts by weight of diethylene glycol, 2 to 20 parts by weight methanol and 18 to 60 parts by weight methylene dichloride.

3. A composition according to claim 2, wherein said solvent system consists essentially of 55 to 65 parts by weight diethylene glycol, 5 to 15 parts by weight methanol and 20 to 40 parts by weight methylenedichloride.

4. A composition for wettable powders according to claim 1, containing in addition up to 30 parts by weight of water, calculated on the other solvents.

5. A composition according to claim 1, wherein the pesticide concentrate comprises 5 to 15 parts by weight of the composition.

6. A composition according to claim 1, wherein said glycol or glycol ether solvent comprises diethylene glycol, ethyleneglycol or ethylene glycol ether.

7. A method for the application of pesticides comprising generating a pesticide fog or mist of particle size less than 50 microns by subjecting the pesticidal composition in accordance with claim 1 to a hot blast of air and forcing the composition through a nozzle to effect thermal evaporation of the solvent and create the pesticide fog or mist.

8. A method according to claim 7 wherein said solvent system consists essentially of 38 to 80 parts by weight diethylene glycol, 2 to 20 parts by weight methanol and 18 to 60 parts by weight methylenedichloride.

9. A method according to claim 7, wherein said composition additionally contains up to 30 parts by weight water, calculated on the other solvents.

10. A method according to claim 7, wherein said glycol or glycol ether solvent comprises diethylene glycol, ethylene glycol or ethylene glycol ether.

* * * * *